United States Patent [19]

Wicks et al.

[11] Patent Number: 4,883,641

[45] Date of Patent: Nov. 28, 1989

[54] CLOSURE AND CONTAINER ASSEMBLY FOR BIOLOGICAL STERILITY INDICATOR

[75] Inventors: James H. Wicks; William E. Foltz, both of St. Paul, Minn.

[73] Assignee: Minnesota Mining and Manufacturing Company, St. Paul, Minn.

[21] Appl. No.: 249,982

[22] Filed: Sep. 27, 1988

Related U.S. Application Data

[63] Continuation-in-part of Ser. No. 66,586, Jun. 26, 1987, abandoned, which is a continuation of Ser. No. 823,535, Jan. 29, 1986, abandoned, which is a continuation of Ser. No. 621,554, Jun. 18, 1984, abandoned.

[51] Int. Cl.$^4$ ............................................. B65D 51/16
[52] U.S. Cl. ........................................ 422/50; 422/58; 422/61; 422/102; 220/366; 215/307; 215/355; 435/31; 435/296; 435/810
[58] Field of Search .................. 422/58, 61, 102, 103, 422/50; 220/366; 215/307, 355; 435/31, 296, 810

[56] References Cited

U.S. PATENT DOCUMENTS

| | | | |
|---|---|---|---|
| 3,661,717 | 5/1972 | Nelson | 435/31 |
| 3,881,626 | 5/1975 | Bartell | 215/307 |
| 4,193,402 | 3/1980 | Rumpler | 215/307 |
| 4,291,122 | 9/1981 | Orelski | 435/31 |
| 4,304,869 | 12/1981 | Dyke | 435/296 |
| 4,416,984 | 11/1983 | Wheeler, Jr. | 435/31 |

FOREIGN PATENT DOCUMENTS 0078112  5/1983  European Pat. Off. .............. 435/31

Primary Examiner—Barry S. Richman
Assistant Examiner—Lynn M. Kummert
Attorney, Agent, or Firm—Donald M. Sell; Walter N. Kirn; Jennie G. Boeder

[57] ABSTRACT

A closure and container assembly biological sterility indicator having a container, a closure, test spores, growth and indicator media, and a frangible barrier for separating the growth medium from the test spores is shown. The closure is moveable in the container between open and closed positions. When in the open position, sterilant may flow into and out of the container via a tortuous pathway defined by the interior surface of the container or the exterior surface of the closure. The tortuous pathway may also include one or more openings in the wall of the closure. When the closure is in the closed position, the container is sealed. The sterility indicator may be assembled with the test spores impregnated on a spore strip which is placed in close proximity to the closure.

15 Claims, 3 Drawing Sheets

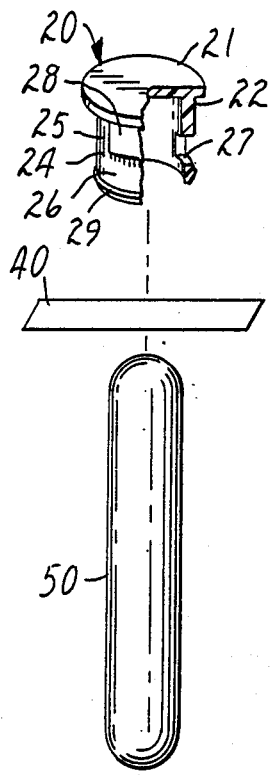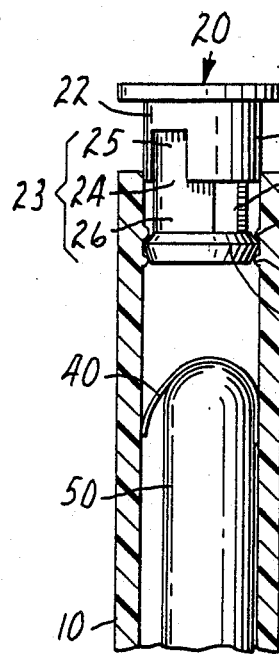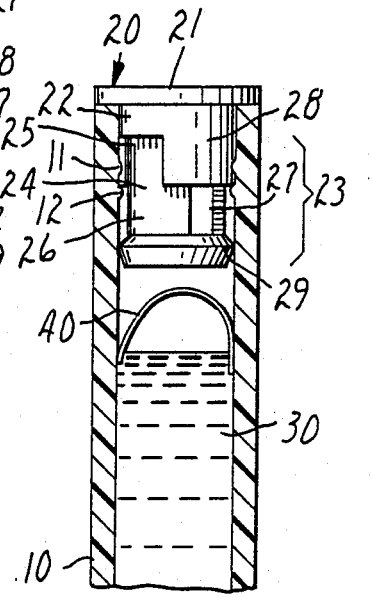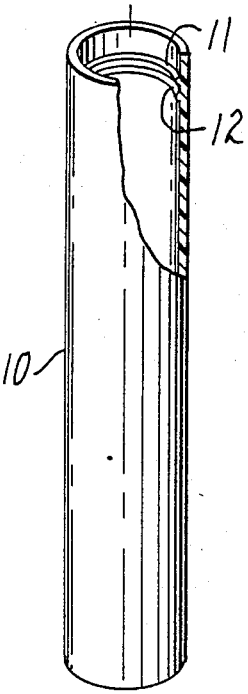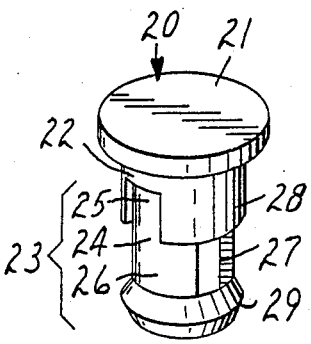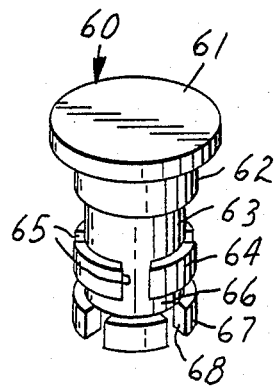
FIG.1  FIG.2  FIG.3  FIG.4  FIG.5

CLOSURE AND CONTAINER ASSEMBLY FOR BIOLOGICAL STERILITY INDICATOR

This application is a continuation-in-part of U.S. Ser. No. 66,586, filed June 26, 1987, now abandoned which was a continuation of U.S. Ser. No. 823,535, filed Jan. 29, 1986, now abandoned, which was a continuation-in-part of U.S. Ser. No. 621,554, filed June 18, 1984, now abandoned.

FIELD OF THE INVENTION

This invention relates to a closure and container assembly for a sterility indicator for determining the efficacy of sterilization of microorganisms. More particularly it relates to a cap and closure assembly adapted for use in sterility indicators used in modern high speed gravity displacement sterilizers commonly known as "flash" sterilizers.

BACKGROUND OF THE INVENTION

Testing of sterilizers for efficacy is standard practice in both the health care field and in industrial usage. Biological indicators such as that described in U.S. Pat. No. 3,661,717 are commonly used. These indicators entail exposing a test population of microbial spores to a sterilant during a sterilizing cycle. Thereafter, the test spores are cultured for an incubation period and tested for viability.

In biological indicators, test organisms are generally used which are many times more resistant to the sterilization process than most organisms encountered in natural contamination. The test organisms should survive during the sterilization process longer than any natural contaminants and then be killed prior to completion of the cycle. With the advent of modern flash sterilizers having cycle times of three minutes, killing of the test organisms in a self contained indicator before completion of the sterilization cycle does not always occur. Ideally, the test organism should be killed in a sterilizer cycle comprised of a short heat up time (1 to 2.5 min.), a three minute cycle, and a very short cool down time (approximately 10 seconds).

The sterility indicator described in Nelson U.S. Pat. No. 3,661,717 is comprised of a container for a test spore strip with an opening at one end. Also in the container is an ampule filled with an aqueous nutrient and indicator system. The container is covered with a gas transmissive, bacterial impermeable closure. In use this indicator is placed within the sterilization chamber during the cycle. During the cycle, sterilant enters the container displacing fluid in the container. Circulation of the sterilant around the spore strip kills the spores. Thereafter the ampule containing the nutrient and indicator media is crushed upon deformation of the outer compartment. When the test strip is disposed beside or below the growth medium ampule, wetting of the test strip upon crushing of the ampule presents no difficulty. However, since the sterility indicator cannot be inverted after crushing the ampule without permitting the growth medium to leak out, placement of the test strip above the ampule and adjacent to the opening of the container to achieve improved exposure to sterilant is not practical.

U.S. Pat. No. 4,304,869 and European Patent Application No. 78,112 (published Apr. 5, 1983) each show a sterility indicator with a cap that permits introduction of sterilant via a tortuous pathway defined by the internal surface of the cap and the external surface of the vial. In this system the sterilant flows upward in the annular space defined by the inner surface of the cap and the outer surface of the vial and is then deflected to flow in the direction opposite to its initial flow to reach the spore strip. The system can be sealed from the environment by depressing the cap to a closed position.

SUMMARY OF THE INVENTION

Applicants have found that use of a container and stopper-like closure assembly wherein the closure is movable between two positions to permit a net forward flow of sterilant into the container during the sterilizing cycle and sealing of the container after the cycle overcomes the disadvantage of the Nelson device noted above and results in significantly improved kill times. By net forward flow it is meant that the assembly is constructed such that the sterilant flow path requires the sterilant to flow at all times in a direction which forms an angle of 90° or less with the major axis of the container. The container and closure assembly of the present invention is used in a system which includes a translucent container having a single opening, a closure, test microbial spores, growth and indicator media, and a frangible barrier for separating the growth medium from the test spores. The container and closure are specially designed to create a tortuous pathway defined by the interior surface of the container, the exterior surface of the closure and may include an opening in the wall of the closure to allow sterilant to flow into and out of the container when the closure is in the open position. The tortuous pathway is sized and shaped so that air traveling across the pathway under positive pressure of 10 mm Hg will displace a 90 ml, 14 cm tall column, of water in a maximum time of 10 seconds. The pathway can conveniently be sized and shaped so that air traveling across the pathway under positive pressure of 10 mm Hg will displace a 90 ml, 14 cm tall column, of water in a maximum time of 6.5 seconds. Preferably the pathway is sized and shaped so that air traveling across the pathway under positive pressure of 10 mm Hg will displace a 90 ml, 14 cm tall column of water in a maximum time of 5.5 seconds.

The tortuous pathway may be defined by a tortuous recess along the interior surface of the container and a continuous or smooth surface along the exterior surface of the closure. Alternatively, the interior surface of the container and the exterior surface of the closure may both have recesses which cooperate when the unit is assembled in the open position to define a tortuous recess. Preferably the tortuous pathway is defined by a smooth or continuous surface on the interior of the container and a recess on the exterior wall of the closure. Each of these tortuous recesses may communicate with an opening in the wall of the closure.

In the preferred container and closure assembly the container is cylindrical with an opening at one end and smooth interior walls adjacent the opening. The closure has two distinct segments defining the open and closed positions. The preferred closure has a substantially cylindrical sealing segment which engages the interior surface of the container walls to seal the unit when the closure is in the closed position. Depending from the sealing segment is a tortuous pathway segment. The tortuous pathway segment includes at least one recess along the exterior wall of the closure which is sufficiently angular or arcuate to impede vector flow of microorganisms. Also included in the tortuous pathway segment of the closure is an opening in the wall of the closure which provides fluid communication between the recess and the interior of the container. Here again, the tortuous pathway is sized and shaped so that air flowing through the tortuous pathway under 10 mm Hg pressure will displace a 90 ml, 14 cm tall column of water in a maximum time of 10 seconds. Conveniently the tortuous pathway is sized and shaped so that air flowing through it under 10 mm Hg pressure will displace a 90 ml, 14 cm tall column of water in a maximum time of 6.5 seconds. Most preferably the tortuous pathway is sized and shaped to permit air flowing through it under 10 mm Hg pressure to displace a 90 ml, 14 cm tall column of water in a maximum time of 5.5 seconds.

Applicants have found that use of a container and closure assembly which permits net forward flow of the sterilant into the container provides significantly faster kill time than achieved with a cap-like closure having a tortuous path requiring a net reversal of flow direction of the sterilant. By net forward flow it is meant that the assembly is constructed such that the sterilant flow path requires the sterilant to flow at all times in a direction which forms an angle of 90° or less with the major axis of the container, that is, an axis running through the center of the container, from its open end to its closed end.

A further aspect of the invention entails placing the test spores in close proximity to the closure. This assembly is appropriate where an exceptionally resistant strain of spores is employed or in any other situation where a kill time faster than achieved with placement of the spore strip below or beside an ampule containing growth medium is desired. In this embodiment of the invention the container is a transparent cylinder having one open end. A frangible ampule containing a growth medium and indicator is inserted in the cylinder. The spore strip is placed on top of the frangible ampule close to the opening of the cylinder. Finally, the stopper-like closure of the present invention is inserted in the opening. When the closure is partially inserted, the sterilant fluid is allowed to enter the container by a tortuous path defined by the interior surface of the container and the exterior surface of the closure. When the closure is fully inserted it seals the container from the environment.

In use a sterility indicator with the container and closure assembly of the present invention is placed within a sterilizing chamber during its cycle with the closure partially inserted. Upon completion of the sterilizing cycle the sterility indicator is removed from the sterilizing chamber and the closure is fully inserted to seal the container. Then the ampule can be crushed, preferably by compressing the sidewalls of the container. When the spore strip is placed adjacent the closure the spore strip is wetted by inverting the sterility indicator. Thereafter, the sterility indicator can be incubated for a time sufficient to culture any viable organisms remaining in the spore strip. The presence of viable organisms will then cause the indicator to change color.

Further understanding of the present invention may be obtained by reference to the following drawings and detailed description.

BRIEF DESCRIPTION OF THE DRAWINGS

FIG. 1 is an exploded assembly view in perspective with portions broken away of a sterility indicator with one embodiment of the container and closure assembly of the present invention;

FIG. 2 is a view in perspective of one embodiment of a closure for use in the present invention;

FIG. 3 is a vertical section of the sterility indicator shown in FIG. 1 with the closure partially inserted;

FIG. 4 is a vertical section of the sterility indicator shown in FIG. 1 with the closure fully inserted; and FIG. 5 is a view in perspective of an alternative construction of a closure for use in the present invention.

DETAILED DESCRIPTION

Figure 6:
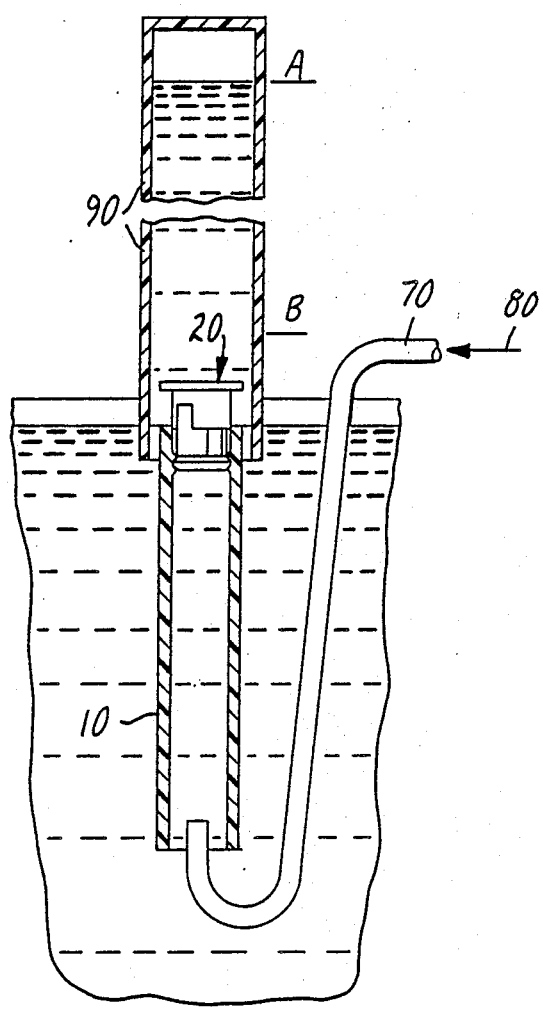
FIG. 6 shows schematically the test unit described in comparative example 2.

Referring now to FIG. 1, the container and closure assembly of the present invention is adapted for use in a sterility indicator comprised of a translucent (including transparent) container 10, a closure 20, test spores preferably impregnated on a test spore strip 40, growth and indicating media 30, and means for separating the growth medium from the spore strip 40, illustrated in FIG. 1 as a frangible ampule 50.

The container 10 is made from a translucent (including transparent) material which will withstand the high temperatures typically encountered in sterilizers. Conventional sterilizers generally reach temperatures on the order of 250° F. (121° C.). Modern flash sterilizers will reach temperatures as high as 270° F. (132° C.). The container can be made by injection molding from any suitable material. Suitable materials include polycarbonate, polypropylenes such as Pro-Fax 6523 (Himont U.S.A., Inc., Wilmington, Del.), and polymethylpentenes such as MX-001 TPX (Mitsui Petrochemical Industries Ltd., Tokyo, Japan). These materials provide the suitable characteristics of translucency (including transparency), so that a color change may be visually observed, and deformability, so that a frangible ampule disposed within the container can be crushed by deformation of the container's walls. Additionally, the walls should be substantially impermeable to gases and liquids. The container is preferably made of polymethylpentene or polypropylene and sized so that an ampule fits in the container without leaving relatively large void spaces in which sterilizing fluids could become entrapped during the sterilizing cycle.

The closure can be made from any material that will withstand the sterilizer temperatures. As in the case of the container suitable materials include polycarbonates, polypropylenes and polymethylpentenes. Polymethylpentene is preferred. Additionally, opaque materials may be used.

The structure of the preferred closure device 20 is most clearly shown in FIG. 2. The closure is broadly comprised of a top 21 and a hollow body open at the bottom which is conveniently described in terms of two functional segments, a sealing segment 22 and a tortuous pathway segment 23. In the embodiment shown, the sealing segment 2 is uppermost immediately adjacent the top 21. It is a substantially cylindrical portion having an outside diameter sized to snugly engage the interior surface of the cylinder 10 when the closure 20 is fully inserted in the container 10 (as shown in FIG. 4), so as to seal the interior of the container from the outside environment.

The tortuous pathway section 23 has at least one and preferably two recessed areas 24 creating a recessed space between the interior surface of the container 10 and the sidewall of the closure. The recess 24 shown in FIG. 22 is comprised of a top portion 25 which encompasses about 15% of the circumference of the closure and a bottom section 26 immediately below the top portion 25 which encompasses about 35% of the circumference of the closure. The bottom portion 26 of the recess communicates at each end with openings 27 in the wall of the closure. Each opening 27 preferably encompasses about 15% of the circumference of the closure. The top portion 25 of the recessed pathway ends on each side at sidewall areas 28 which are sized to snugly engage the interior wall of container 10 as shown in FIG. 3. Preferably the closure has two tortuous recesses symmetrically arranged around the circumference of the closure.

The tortuous pathway segment ends with an annular ring 29 depending from the lower part 26 of the recessed pathway section 24. The annular ring 29 is preferably sized with its widest outside diameter sufficiently large to snugly engage the interior surface of the container 10. The container 10 may conveniently be provided with an inwardly projecting flange 11 to engage the surface of the ring 29. Additionally a second flange 12 may be provided to hold the closure 20 open to a desired position during the sterilizing cycle. Upon completion of the cycle the closure 20 may be fully inserted by depressing it to force the ring 29 past flange 12.

When the closure 20 is partially inserted in the container 10 (as shown in FIG. 3), fluid may enter the container 10 by flowing in the space created by the recessed space 24 and the interior wall of the container 10. When the sterilant passes through the lower portion 26 of the recessed space 24 it reaches the annular ring 29, or the inwardly projecting flange 11 when it is used, and is laterally deflected along the interior surface of the container 10 and the exterior surface of the closure to the openings 27 where it enters the container.

Applicants have observed significantly improved flow rates of fluid through the tortuous pathway with the container and closure of the present invention where the container is a cylinder having an inside length of about 1.9 inch (4.8 cm) and an inside diameter of about 0.3 inch (0.76 cm). The closure has an overall length of about 0.3 inch (0.76 cm). The sealing segment is about 0.05 inch (0.13 cm) long and has an outside diameter of about 0.3 inch (0.76 cm). The tortuous pathway segment 23 has two recessed areas 24 symmetrically disposed around the closure. The top portion 25 of each recessed area encompasses 15% of the circumference and is about 0.1 inch (0.25 cm) long and 0.04 inch (0.1 cm) deep. Interposed between these top recessed portions 25 are sidewalls 28 with an outside diameter of about 0.3 inch (0.76 cm). The bottom portion 26 of each recessed area 24 encompasses 35% of the circumference and is also about 0.1 inch (0.25 cm) long and 0.04 inch (0.1 cm) deep. Interposed between the two bottom portions 26 are two windows 27 which each encompass 15% of the circumference and are about 0.1 inch (0.25 cm) tall. A sterility indicator having the container and closure assembly built to these dimensions was tested for flow rates of air across the tortuous pathway. The test and results are described below in Comparative Example 2.

The nutrient and indicator media preferably are contained in a frangible glass ampule 50. Conventional nutrient media such as Tryptic Soy Broth (a product of Difco Laboratory, Detroit, Mich.) may be used. The indicator may be a pH indicator such as brom cresol purple, bromothymol blue, phenol red, and the like; alternatively oxidation reduction dye indicators such as methylene blue may be used.

The test microorganisms are preferably bacterial or fungal spores impregnated in a substrate. To assure reproducibility the approximate number of microorganisms should be predetermined. This is readily accomplished by preparing an aqueous suspension with a known volumetric microorganism concentration and thereafter moistening a substrate (e.g., high quality filter or chromatography paper) with a precise aliquot of the suspension and allowing it to dry. The preferred spore strip contains approximately $1.0 \times 10^5$ to $2.0 \times 10^6$ CFU. The preferred microorganisms are *Bacillus stearothermophilus* (for use in steam sterilizers). Applicants have found that when the spore strip is placed on top of the nutrient and indicator ampule 50 and immediately below the opening of the cylinder 10, kill times of about three minutes can be obtained when tested in a 132° C. (270° F.) flash sterilizer.

The foregoing description is directed to Applicants, preferred embodiment. Many variations of the foregoing system are possible which will nonetheless fall within the scope of the present invention. For example, the closure may include an ampule crushing device as shown in U.S. Pat. No. 4,304,869 wherein the container has a decreasing diameter and the closure has tabs depending from the bottom of the closure device which upon depression of the closure device serve to crush the ampule. Similarly the container and closure assembly of the present invention may be used in a system having an ampule crushing pin disposed in the bottom of the container.

An alternative configuration of the closure is shown in FIG. 5. This closure 60 has a top 61 and depending sidewalls. The first depending section of the sidewall 62 is sized to snugly engage the interior surface of the container and seal the container when the closure is fully inserted. The next depending segment 63 of the sidewall has a diameter sufficiently small to create an annular space between the sidewall of the container and the closure. The next depending segment 64 has a diameter sized to engage the sidewalls of the container with cutaway segments 65 to allow fluid communication between segment 63 and segment 66 which depends from segment 64. Segment 66 is sized to create an annular space between the interior surface of the container and the closure. Depending from segment 66 is segment 67 which like segment 64 has a diameter sized to engage the interior surface of the container and cutaway portions 68 to allow fluid communication. The cutaway portions 68 are staggered so that they do not fall below cutaway portions 65 of segment 64. In use sterilant flowing down into the container is deflected laterally by the alternating segments having cutaway portions while it is permitted to flow at all times in a direction which forms an angle of 90° or less with the major axis of the container.

Figure 7:
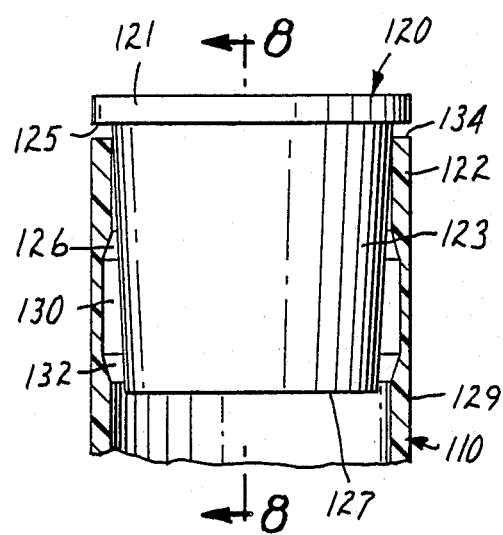
FIG. 7 is a side cross sectional view of a modified embodiment showing the top portion of the container with the closure partially inserted therein.

FIG. 7 illustrates an alternative embodiment of the present invention wherein the tortuous pathway is defined by the exterior wall of the closure 120 and recesses on the interior wall of the container 110. The closure 120 has a cap 121 and circular sidewalls 123. The sidewalls are preferably tapered slightly inward such that the diameter of the closure taken through the sidewalls is larger at the portion adjacent the cap 121 than at the bottom 127 of the closure. The diameter of cap 121 is greater than the diameter of the closure at any point along its sidewalls 123, by at least twice the depth of top recessed area 124, described hereinbelow. The cap includes ledge 125 which is at least as wide as the depth of top recessed area 124.

Figure 8:
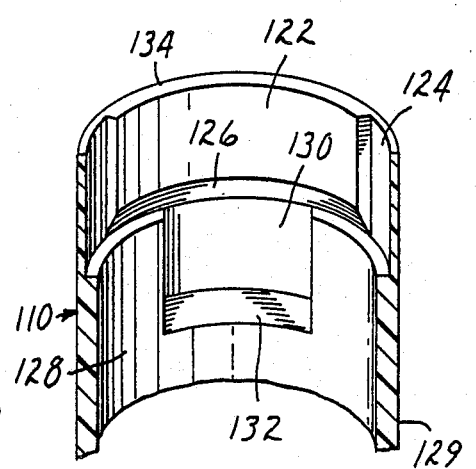
FIG. 8 is a sectional view of the top interior of the container along line 8—8 of FIG. 7, with closure removed.

The recessed interior surface of the container 110 is most clearly shown in FIG. 8. A top segment 122 is uppermost immediately adjacent the opening in the container 110. It is a substantially cylindrical portion having an inside diameter sized to engage the exterior sidewalls of cap 120, as best illustrated by FIG. 7. Cut within segment 122 is at least one and preferably two top recessed areas 124, which each encompass about 15% of the circumference of the interior surface of container 110. Recessed area 124 is dimensioned to create a space between it and sidewalls 123 of the closure 120.

Immediately below top segment 122 and communicating with top recessed areas 124 at the bottom portion thereof are second recessed areas 126 each of which encompass about 35% of the circumference of the interior of container 110. Preferably, as shown in FIGS. 7 and 8 the interior walls of container 110 which depend from top segment 122 and which define second recess 126 lie at an angle of about 130° with the exterior wall 129 of container 110. Recessed areas 126 in combination with the bottom portion of top recessed areas 124 create an annular space between the sidewalls 123 of the closure 120 and the interior surface of the container, and allow fluid communication between recessed area 124 and third recessed area 130 which depends from recessed area 126.

Depending from second recessed area 126 is bottom segment 128 which has a diameter equal to the diameter of top segment 122. Cut within bottom segment 128 is one, and preferably two third recessed areas 130 which each encompass about 15% of the circumference of the interior surface of container 110. The third recessed areas 130 are staggered so that they do not fall below top recessed areas 124, and the third recessed areas 130 are in fluid communication with second recessed areas 126.

Immediately below third recessed areas 130 are fourth recessed areas 132 which, like third recessed areas 130, each encompass about 15% of the circumference of the interior surface of container 110. As shown in FIGS. 7 and 8 the interior walls of container 110 which depend from third recessed areas 130 and which define fourth recessed areas 132, lie at an angle of about 130° with the exterior wall 129 of container 110, and are angled inward towards the center of container 110 so that at its lowermost portion, recessed area 132 has a diameter equal to that of bottom segment 128.

When the closure 120 is partially inserted in the container 110 (as shown in FIG. 7) and the sterility indicator is placed in a sterilizer, sterilizing fluid or gas may enter the container 110 by flowing in the space created between top recessed areas 124 and the sidewalls 123 of closure 120. The fluid then is directed at a 90° angle and flows laterally through second recessed area 126. When the fluid reaches third recessed area 130 it is again diverted 90° to flow in a direction parallel to the major axis of container 110. The fluid then flows over fourth recessed area 132 where it enters the remainder of container 110. Upon completion of the sterilization cycle, the closure 120 may be fully inserted by depressing it to force ledge 125 in contact with the upper surface 134 of container 110. The ledge 125 will then cover the space between top recessed area 124 and the sidewalls 123 of the closure, thereby sealing the container 110. These and other variations are intended to fall within the scope of the claims that follow.

COMPARATIVE EXAMPLE 1

A sterility indicator constructed in accordance with the present invention with a stopper-like closure was compared to a sterility indicator having a cap-like closure where the tortuous path requires the sterilant to reverse its flow. The cap and container assembly of the sterility indicators of American Sterilizer Company shown in the U.S. Pat. No. 4,304,869 were used in the comparative experiment. In each instance identical growth media of trypticase soy broth (Baltimore Biological Laboratories) and phenol red indicator (Sigma Chemical Company) were used. The spore strip used in each instance was impregnated with $1.1 \times 10^6$ CFU of *Bacillus stearothermophilus*. The sterility indicators were assembled with the spore strip positioned along the side of the ampule. The test system was a Joslyn BIER Vessel of the gravity displacement type operating at 270° F. (132° C.).

Incremental exposure times of 3.0, 3.5, 4.0, 4.5, 5.0, 5.5, 6.0 and 6.5 minutes were used. Twenty indicators of each type were tested at each exposure time. Readings were made after incubating 48 hours. The test results are summarized below where D-value is the time required to destroy 90% of the cells calculated on a population of $1.1 \times 10^6$ CFU. The sterility indicators having the container and closure assembly of the present invention yield a D-value of 0.61 while the 100 indicators tested at exposure times of 3.5 minutes to 5.5 minutes yielded 41% positive results. The sterility indicators having the container and cap assembly shown in U.S. Pat. No. 4,304,869 yielded a D-value of 0.83 while the 100 indicators tested at exposure time of 3.5 minutes to 5.5 minutes yielded 73% positive results.

| Exposure Time | Number of Positive Cultures | |
|---|---|---|
| | Present Invention | Cap Closure Pat. No. 4,304,869 |
| 3.0 | 20 | 20 |
| 3.5 | 20 | 20 |
| 4.0 | 20 | 20 |
| 4.5 | 1 | 20 |
| 5.0 | 0 | 13 |
| 5.5 | 0 | 0 |
| 6.0 | 0 | 2 |
| 6.5 | — | 0 |

COMPARATIVE EXAMPLE 2

The container and closure assembly of the present invention was tested for fluid velocity through the tortuous pathway and compared to the cap and closure assembly of the American Sterilizer Company indicator shown in U.S. Pat. No. 4,304,869. For each assembly the bottom of the container 10 was drilled out and the container was attached to vacuum tubing 70. The vacuum tubing was in turn connected to a source 80 of air flowing under 10 mm Hg pressure. With the closure 20 in the open position, the assembly was placed in a tank of water at the bottom of a 6.43 cm in cross section diameter cylindrical column 90 of water extending 8 inches (20 cm) above the surface of the water in the tank shown as dimension "A" in FIG. 6. Thereafter, air was allowed to flow through vacuum tubing 70, the container 10, and across the tortuous pathway at a positive pressure of 10 mm Hg. The time required to displace a 90 ml, 14 cm column of water (leaving a 6 cm column of water shown as dimension "B" in FIG. 6) was measured. The experiment was repeated two more times for each closure and three assemblies of each style were tested. The times for the container and closure of the present invention ranged from 4.0 seconds to 6.0 seconds. The average of all times for the assembly of the present invention was 4.9 seconds. The time for the container and cap assembly shown in U.S. Pat. No. 4,304,869 ranged from 12.0 seconds to 28.0 seconds. The average for all times for that assembly was 18.8 seconds.

We claim:

1. A closure and container assembly comprising a closure having a top and a depending sidewall, and a container having an interior surface and an opening for receiving the closure, wherein the closure is movable between two positions within the container such that when in the first position the container is sealed and when in the second position fluid communication exists between an environment outside of the container and the interior of the container via a tortuous pathway defined by at least one recess along the interior surface of the container or the exterior surface of the sidewall of the closure which tortuous pathway is constructed and arranged to cause at least two deflections of a fluid entering the container and to require that said fluid entering the container flow in a direction which forms an angle of 90° or less with an axis running through the center of said container, from said opening to the bottom of said container, to displace fluid in the container and is sized and shaped to accommodate a rapid rate of flow therethrough so that when tested to determine the flow resistance thereof, in a test wherein a hole is drilled in said bottom of said container and the hole is connected to a source of air, upon forcing air from the source of air through the container across the tortuous pathway, when the closure is in its second position and the assembly is placed in a tank of water at the bottom of a 20 cm column of water extending above the surface of the water in the tank, the air flowing across the tortuous pathway and into the column of water under 10 mm Hg pressure will displace a 90 ml, 14 cm column of water in a maximum time of 10 seconds.

2. The assembly of claim 1 wherein the tortuous pathway further comprises at least one opening in the sidewall of the closure.

3. The assembly of claim 1 wherein the closure has a sealing segment formed on the exterior surface of the sidewall and having an outside diameter sized to snugly engage the interior surface of the container when the closure is in the first sealing position.

4. The assembly of claim 1 wherein the tortuous pathway is sized and shaped so that when said test is conducted, air flowing across the tortuous pathway and into the column of water under 10 mm Hg pressure will displace a 90 ml, 14 cm column of water in a maximum time of 6.5 seconds.

5. The assembly of claim 1 wherein the tortuous pathway is sized and shaped so that when said test is conducted air flowing across the tortuous pathway and into the column of water under 10 mm Hg pressure will displace a 90 ml, 14 cm column of water in a maximum time of 5.5 seconds.

6. The closure and container assembly of claim 1 further comprising a spore strip having coated on its surface test microbial spores which spore strip is positioned within the container in close proximity to the closure.

7. A closure and container assembly comprising a closure and container wherein the container is a transparent cylinder having an interior surface and an opening at one end and the closure has a top and depending sidewalls, and the depending sidewalls have a sealing segment comprised of a substantially cylindrical exterior surface of the sidewall adapted to snugly engage the interior surface of the container and seal the container when the closure is fully inserted, and a tortuous pathway segment depending from the sealing segment and having at least one tortuous recess along its exterior surface and at least one opening contiguous with at least one end of each such recess such that when the closure is partially inserted the tortuous pathway segment and the interior surface of the container define a tortuous pathway for fluids to enter and exit the container, said tortuous pathway constructed and arranged to cause at least two deflections of a fluid entering the container and to require that said fluid entering the conttainer flow in a direction which forms an angle of 90° or less with an axis running through the center of said container, from said opening to the bottom of said container, to displace fluid in the container and is sized and shaped to accommodate a rapid rate of flow therethrough so that when tested to determine the flow resistance thereof, in a test wherein a hole is drilled in said bottom of said container and the hole is connected to a source of air, upon forcing air from the source of air through the container across the tortuous pathway, when the closure is partially inserted in said container and the assembly is placed in a tank of water at the bottom of a 20 cm column of water extending above the surface of the water in the tank, the air flowing across the tortuous pathway and into the column of water under 10 mm Hg pressure will displace a 90 ml, 14 cm column of water in a maximum time of 10 seconds.

8. The assembly of claim 1 wherein the tortuous pathway segment of the closure has two tortuous recesses symmetrically disposed around its circumference and two openings in the sidewall of the closure interposed between the two tortuous recesses such that each opening communicates with each recess.

9. The closure and container assembly of claim 8 further comprising a spore strip having coated on its surface test microbial spores which spore strip is positioned within the container in close proximity to the closure.

10. The assembly of claim 7 wherein the tortuous recess is sized and shaped so that when said test is conducted air flowing across the tortuous recess and into the column of water under 10 mm Hg pressure will displace a 90 ml, 14 cm column of water in a maximum time of 6.5 seconds.

11. The assembly of claim 7 wherein the tortuous pathway is sized and shaped so that when said test is conducted air flowing across the tortuous recess and into the column of water under 10 mm Hg pressure will displace a 90 ml, 14 cm column of water in a maximum time of 5.5 seconds.

12. The closure and container assembly of claim 7 further comprising a spore strip having coated on its surface test microbial spores which spore strip is positioned within the container in close proximity to the closure.

13. A closure and container assembly comprising a closure and container wherein the container is a transparent cylinder having an interior surface and an opening at one end and the closure has a top and depending sidewalls, and the container has adjacent its opening and on its interior walls an engaging segment comprised of a substantially cylindrical interior surface of the container sized to include a major portion which is capable of snugly engaging the exterior surface of the sidewalls of the closure when the closure is partially inserted in the container, and a tortuous pathway segment cut within the engaging segment and having at least one tortuous recess along its interior surface, at least one opening contiguous with at least one end of said recess such that when the closure is partially inserted the tortuous pathway segment and the exterior surface of the sidewalls of the closure define a tortuous pathway for fluids to enter and exit the container, said tortuous pathway constructed and arranged to require that said fluid entering the container flow in a direction which forms an angle of 90° or less with an axis running through the center of said container, from said opening to the bottom of said container, to displace fluid in the container and is sized and shaped to accommodate a rapid rate of flow therethrough so that when tested to determine the flow resistance thereof, in a test wherein a hole is drilled in the bottom of said container and the hole is connected to a source of air, upon forcing air from the source of air through the container across the tortuous pathway, when the closure is partially inserted in said container and the assembly is placed in a tank of water at the bottom of a 20 cm column of water extending above the surface of the water in the tank, the air flowing across the tortuous pathway and into the column of water under 10 mm Hg pressure will displace a 90 ml, 14 cm column of water in a maximum time of 10 seconds, and a covering portion on the closure which is adapted to cover at least one of the openings and seal the container when the closure is fully inserted therein.

14. The assembly of claim 13 wherein the tortuous pathway segment cut within the engaging segment has two tortuous recesses symmetrically disposed around its circumference and the openings contiguous with each end of each recess are also cut within the engaging segment at the top and bottom of each recess.

15. The assembly of claim 13 wherein the tortuous recess is sized and shaped so that when said test is conducted air flowing across the tortuous recess and into the column of water under 10 mm Hg pressure will displace a 90 ml, 14 cm column of water in a maximum time of 5.5 seconds.

* * * * *